(12) United States Patent
Usuda

(10) Patent No.: US 11,978,550 B2
(45) Date of Patent: May 7, 2024

(54) ENDOSCOPIC IMAGE LEARNING DEVICE, ENDOSCOPIC IMAGE LEARNING METHOD, ENDOSCOPIC IMAGE LEARNING PROGRAM, AND ENDOSCOPIC IMAGE RECOGNITION DEVICE

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/885,568

(22) Filed: Aug. 11, 2022

(65) Prior Publication Data

US 2022/0383607 A1    Dec. 1, 2022

Related U.S. Application Data

(63) Continuation of application No. 16/808,409, filed on Mar. 4, 2020, now Pat. No. 11,450,079.

(30) Foreign Application Priority Data

Mar. 8, 2019    (JP) .................................. 2019-042740

(51) Int. Cl.
*G06V 10/147*    (2022.01)
*A61B 1/00*    (2006.01)
(Continued)

(52) U.S. Cl.
CPC .......... *G16H 30/40* (2018.01); *A61B 1/00009* (2013.01); *A61B 1/000094* (2022.02);
(Continued)

(58) Field of Classification Search
CPC .......... A61B 1/00009; A61B 1/000094; A61B 1/000096; A61B 1/0005; A61B 1/0655;
(Continued)

(56) References Cited

U.S. PATENT DOCUMENTS

2009/0088634 A1    4/2009    Zhao et al.
2012/0294498 A1 *    11/2012    Popovic ............... A61B 1/0005
                                                        382/128
(Continued)

FOREIGN PATENT DOCUMENTS

CN    108550151 A  *  9/2018    ............... G06T 5/50
JP    2011214903       10/2011
(Continued)

OTHER PUBLICATIONS

"Notice of Reasons for Refusal of Japan Counterpart Application", dated May 31, 2023, with English translation thereof, p. 1-p. 8.
(Continued)

*Primary Examiner* — Mekonen T Bekele
(74) *Attorney, Agent, or Firm* — JCIPRNET

(57) ABSTRACT

An object is to provide an endoscopic image learning device, an endoscopic image learning method, an endoscopic image learning program, and an endoscopic image recognition device that appropriately learn a learning model for image recognition for recognizing an endoscopic image in which a treatment tool for an endoscope appears.

The object is achieved by an endoscopic image learning device including an image generation unit and a machine learning unit. The image generation unit generates a superimposed image where a foreground image in which a treatment tool for an endoscope is extracted is superimposed on a background-endoscopic image serving as a background of the foreground image, and the machine learning unit performs the learning of a learning model for image recognition using the superimposed image.

19 Claims, 14 Drawing Sheets

(51) Int. Cl.
*A61B 1/06* (2006.01)
*G06F 18/214* (2023.01)
*G06N 20/00* (2019.01)
*G06V 10/774* (2022.01)
*G16H 30/40* (2018.01)

(52) U.S. Cl.
CPC ...... *A61B 1/000096* (2022.02); *A61B 1/0005* (2013.01); *A61B 1/0655* (2022.02); *G06F 18/214* (2023.01); *G06N 20/00* (2019.01); *G06V 10/774* (2022.01); *A61B 1/063* (2013.01)

(58) Field of Classification Search
CPC ...... A61B 1/063; G06F 18/214; G06N 20/00; G06N 3/045; G06N 3/084; G06N 20/10; G06V 10/774; G06V 2201/034; G16H 30/20; G16H 50/20
See application file for complete search history.

(56) References Cited

U.S. PATENT DOCUMENTS

| | | | |
|---|---|---|---|
| 2015/0190204 A1* | 7/2015 | Popovi | A61B 34/10 600/424 |
| 2019/0206053 A1 | 7/2019 | Ichiki | |
| 2020/0005472 A1 | 1/2020 | Terunuma et al. | |
| 2020/0069160 A1* | 3/2020 | Oosake | A61B 1/000094 |

FOREIGN PATENT DOCUMENTS

| | | |
|---|---|---|
| WO | 2018003503 | 1/2018 |
| WO | 2018159775 | 9/2018 |
| WO | 2018221033 | 12/2018 |

OTHER PUBLICATIONS

"Final Office Action of Japan Counterpart Application", dated Dec. 15, 2023, with English translation thereof, pp. 1-6.

* cited by examiner

FIG. 11
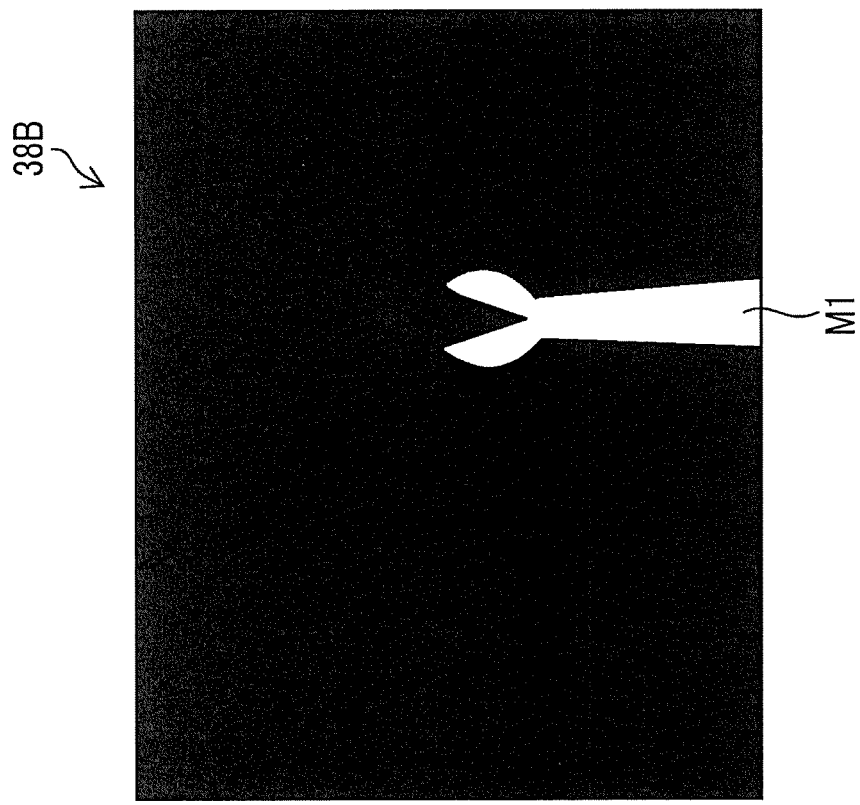
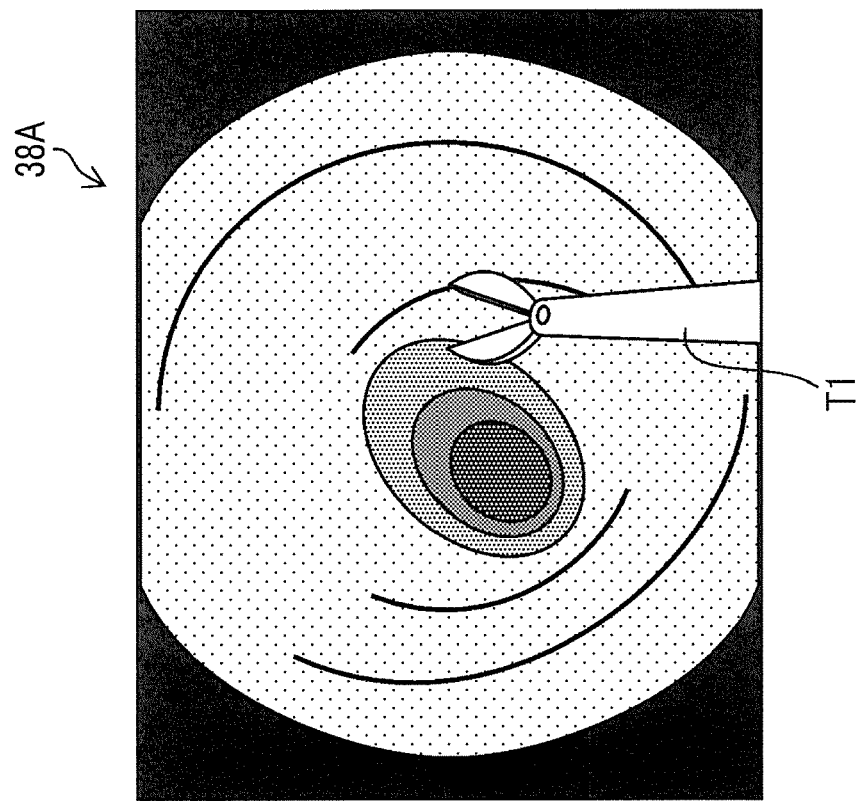

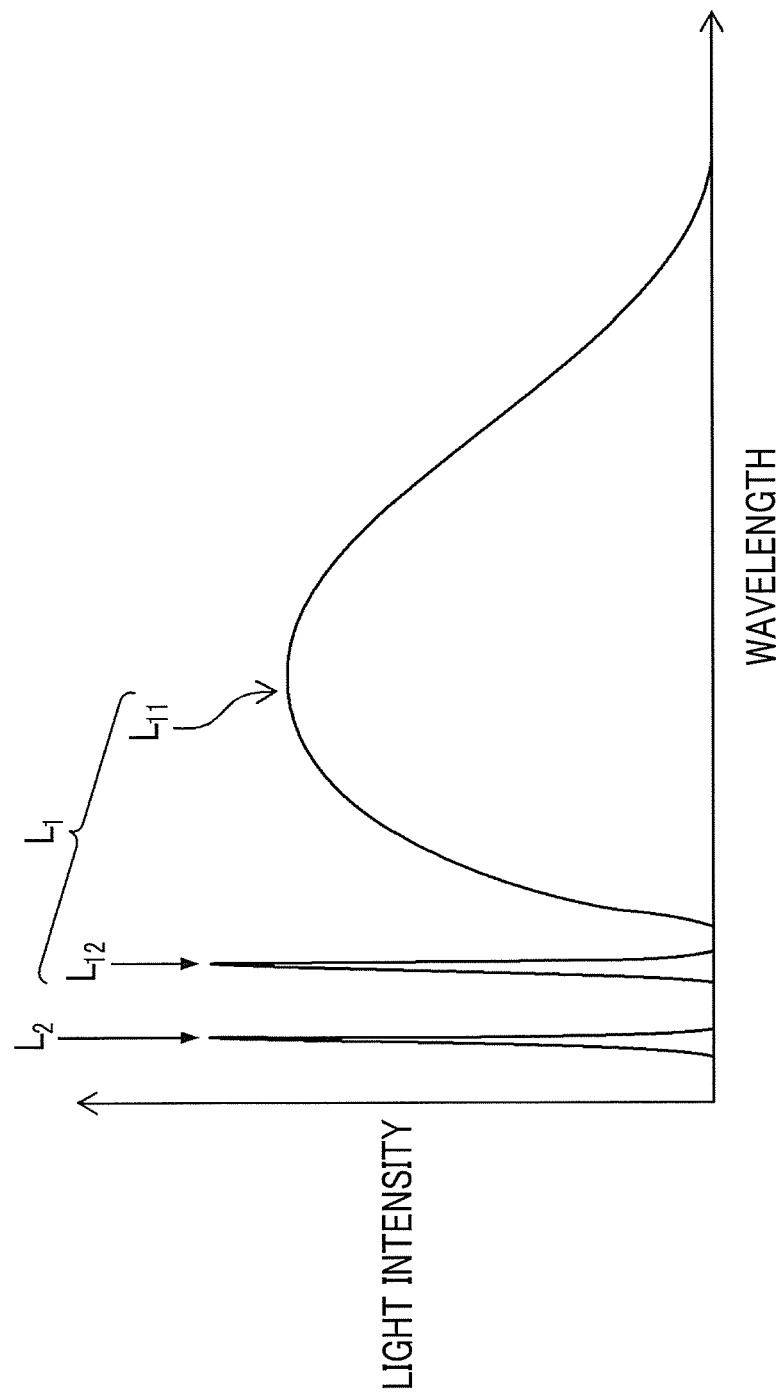

ENDOSCOPIC IMAGE LEARNING DEVICE, ENDOSCOPIC IMAGE LEARNING METHOD, ENDOSCOPIC IMAGE LEARNING PROGRAM, AND ENDOSCOPIC IMAGE RECOGNITION DEVICE

CROSS-REFERENCE TO RELATED APPLICATIONS

This application is a continuation application of and claims the priority benefit of a prior application Ser. No. 16/808,409, filed on Mar. 4, 2020, now allowed, which claims priority under 35 U.S.C. § 119 to Japanese Patent Application No. 2019-042740, filed on Mar. 8, 2019. The entirety of the above-mentioned patent application is hereby incorporated by reference herein and made a part of this specification.

BACKGROUND OF THE INVENTION

1. Field of the Invention

The present invention relates to an endoscopic image learning device, an endoscopic image learning method, an endoscopic image learning program, and an endoscopic image recognition device, and more particularly, to a technique that performs the learning of a learning model for recognizing an endoscopic image.

2. Description of the Related Art

In recent years, deep learning using a multi-layer neural network has attracted attention as one field of machine learning. Particularly, performance exceeding the discrimination ability of the human is being realized in the field of image recognition.

A technique for recognizing an endoscopic image using the deep learning is devised. For example, JP2019-013461A discloses a technique for automatically making a classifier for endoscopic images by a convolution neural network using learning-endoscopic images that are linked to histopathological diagnosis.

SUMMARY OF THE INVENTION

A decisive factor for improving accuracy in the learning of a recognizer using deep learning is to learn using a large number of various learning data. However, it is difficult to ensure the amount of image data and the diversity of image data in the image recognition in a medical field due to a difficulty in collecting image data.

For example, to recognize the use of a treatment tool for an endoscope with high accuracy, it is necessary to correct images using various treatment tools for an endoscope that are available in the market. However, since the collection of a large number of those images is related to intervention in the medical practice, it is difficult to collect a large number of those images. Further, since dozens of kinds of treatment tools for an endoscope are available in the market, it is difficult to collect a large number of learning data for all the treatment tools for an endoscope.

The invention has been made in consideration of the above-mentioned circumstances, and an object of the invention is to provide an endoscopic image learning device, an endoscopic image learning method, an endoscopic image learning program, and an endoscopic image recognition device that appropriately learn a learning model for image recognition for recognizing an endoscopic image in which a treatment tool for an endoscope appears.

To achieve the object, an endoscopic image learning device according to an aspect comprises: an image generation unit that generates a superimposed image where a foreground image in which a treatment tool for an endoscope is extracted is superimposed on a background-endoscopic image serving as a background of the foreground image; and a machine learning unit that performs learning of a learning model for image recognition using the superimposed image.

According to this aspect, the learning of the learning model for image recognition is performed using the superimposed image where the foreground image in which a treatment tool for an endoscope is extracted is superimposed on the background-endoscopic image serving as the background of the foreground image. Accordingly, it is possible to appropriately learn a learning model for image recognition for recognizing an endoscopic image in which a treatment tool for an endoscope appears.

It is preferable that the endoscopic image learning device further comprises a foreground image acquisition unit which acquires the foreground image and a background image acquisition unit acquiring the background-endoscopic image. Accordingly, the foreground image and the background-endoscopic image can be appropriately acquired.

It is preferable that the endoscopic image learning device further comprises a learning-endoscopic image acquisition unit which acquires a learning-endoscopic image and the machine learning unit performs the learning using the learning-endoscopic image. Since the learning model is learned using not only the superimposed image but also the learning-endoscopic image, the learning model can be appropriately learned.

It is preferable that the endoscopic image learning device further comprises an image processing section which performs specific processing on the foreground image. It is preferable that the specific processing is at least one of affine transformation processing, color conversion processing, or noise application processing. Accordingly, an appropriate foreground image can be used.

It is preferable that the endoscopic image learning device further comprises a foreground-material image acquisition section which acquires a foreground-material image including the treatment tool for an endoscope and an image cut-out section which cuts out the treatment tool for an endoscope from the foreground-material image to generate the foreground image. Accordingly, an appropriate foreground image can be used.

It is preferable that the foreground-material image is an endoscopic image which is picked up in a case where the treatment tool for an endoscope is used in an endoscope apparatus. Further, the foreground-material image may be an image other than an endoscopic image. Accordingly, an appropriate foreground image can be generated.

It is preferable that the learning model is at least one of a learning model for recognizing whether or not the treatment tool for an endoscope is present, a learning model for recognizing a type of the treatment tool for an endoscope, a learning model for distinguishing a region of the treatment tool for an endoscope from a region other than the region of the treatment tool for an endoscope, a learning model for detecting a position of a region of interest, or a learning model for classifying an image. According to this aspect, the learning of various learning models for image recognition can be performed.

It is preferable that the machine learning unit performs the learning using a convolution neural network. Accordingly, the learning model can be appropriately learned.

To achieve the object, an endoscopic image recognition device according to another aspect comprises: an image acquisition unit that acquires an endoscopic image; and an image recognition unit that recognizes the endoscopic image acquired by the image acquisition unit by using a learning model learned by the endoscopic image learning device.

According to this aspect, an endoscopic image in which the treatment tool for an endoscope appears can be appropriately recognized.

To achieve the object, an endoscopic image learning method according to still another aspect comprises: generating a superimposed image where a foreground image in which a treatment tool for an endoscope is extracted is superimposed on a background-endoscopic image serving as a background of the foreground image; and performing learning of a learning model for image recognition using the superimposed image.

According to this aspect, the learning of the learning model for image recognition is performed using the superimposed image where the foreground image in which a treatment tool for an endoscope is extracted is superimposed on the background-endoscopic image serving as the background of the foreground image. Accordingly, it is possible to appropriately learn a learning model for image recognition for recognizing an endoscopic image in which a treatment tool for an endoscope appears.

A program causing a computer to perform the endoscopic image learning method is also included in this aspect.

According to the invention, it is possible to appropriately learn a learning model for image recognition for recognizing an endoscopic image in which a treatment tool for an endoscope appears.

BRIEF DESCRIPTION OF THE DRAWINGS

FIG. 11 is a diagram showing a superimposed image 38A and correct answer data 38B of the superimposed image 38A in the case of a learning model for recognizing the segmentation of a treatment tool.

FIG. 16 is a graph showing the intensity distribution of light L1 and light L2.

DESCRIPTION OF THE PREFERRED EMBODIMENTS

Preferred embodiments of the invention will be described in detail below with reference to the accompanying drawings.

Hardware Configuration of Endoscopic Image Learning Device

Figure 1:
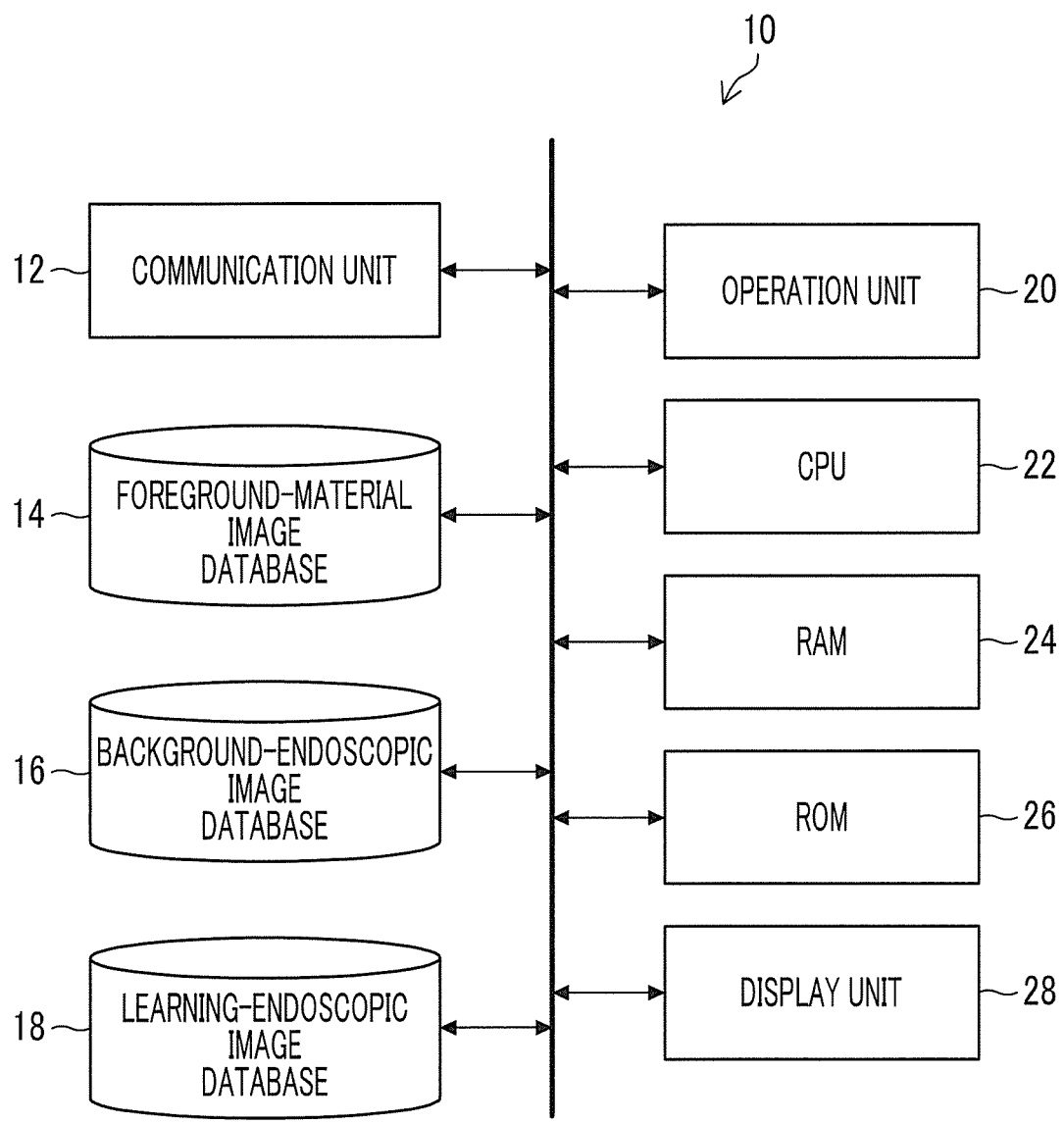
FIG. 1 is a block diagram showing an example of the hardware configuration of an endoscopic image learning device.

An endoscopic image learning device according to an embodiment of the invention is a device that appropriately performs the learning of a learning model by padding learning data used to learn a learning model for recognizing an endoscopic image. FIG. 1 is a block diagram showing an example of the hardware configuration of an endoscopic image learning device.

An endoscopic image learning device 10 is formed of a personal computer or a workstation. The endoscopic image learning device 10 includes a communication unit 12, a foreground-material image database 14, a background-endoscopic image database 16, a learning-endoscopic image database 18, an operation unit 20, a central processing unit (CPU) 22, a random access memory (RAM) 24, a read only memory (ROM) 26, and a display unit 28.

The communication unit 12 is an interface that performs processing for communicating with an external device by wire or radio to exchange information with the external device.

The foreground-material image database 14 is a mass storage device that stores a plurality of foreground-material images 14A in which a treatment tool for an endoscope (hereinafter, referred to as a treatment tool) appears. The treatment tool includes a pair of biopsy forceps, a snare, a diathermy knife, a pair of major forceps, and a hemostatic clip that protrude from a forceps outlet 105 (see FIG. 14). Further, the treatment tool includes a cap 102F (see FIG. 13) that is to be mounted on a distal end part 102D of an endoscope 102. The treatment tool may include other instruments that are likely to appear in an endoscopic image. The foreground-material image database 14 may store information, which represents the types of treatment tools appearing in images, in association with the foreground-material images as necessary.

Figure 2:
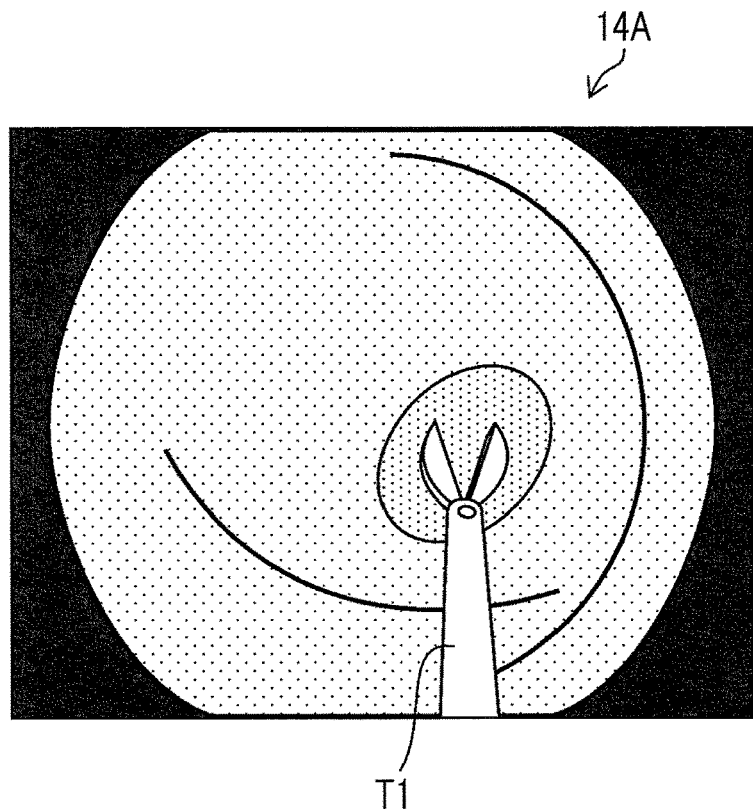
FIG. 2 is a diagram showing an example of a foreground-material image 14A.

FIG. 2 is a diagram showing an example of the foreground-material image 14A. The foreground-material image 14A shown in FIG. 2 is an image that is picked up in a case where a treatment tool is used while a living body is observed using an endoscope, and is an image where a treatment tool T1, which is a pair of biopsy forceps protruding from the forceps outlet 105 (see FIG. 14), appears.

Figure 3:
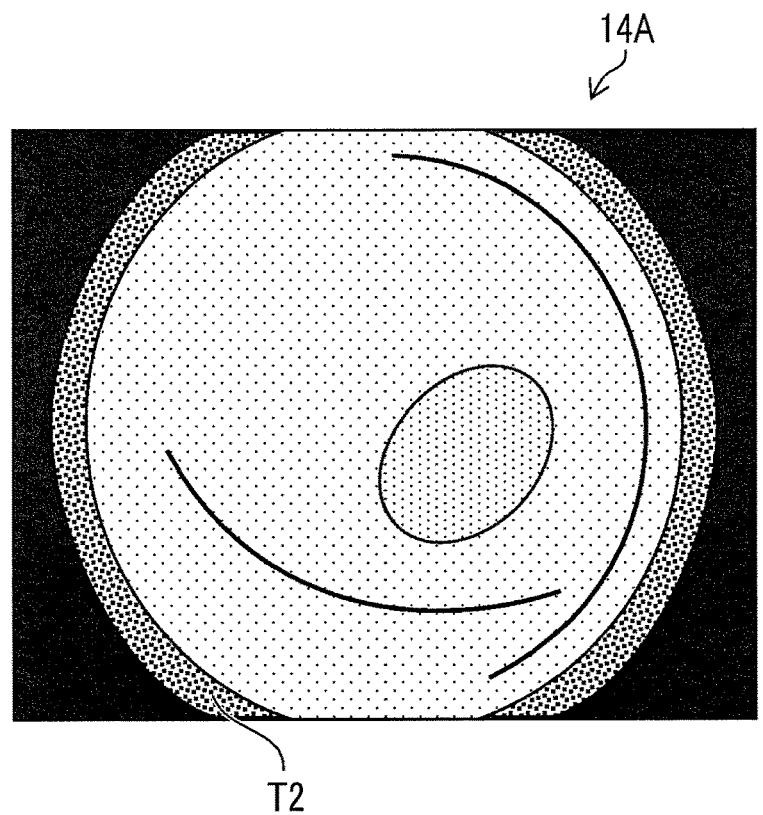
FIG. 3 is a diagram showing another example of the foreground-material image 14A.

FIG. 3 is a diagram showing another example of the foreground-material image 14A. The foreground-material image 14A shown in FIG. 3 is an image that is picked up in a case where a treatment tool is used while a living body is observed using an endoscope, and is an image where a treatment tool T2, which is a cap mounted on the distal end part, appears.

Returning to the description of FIG. 1, the background-endoscopic image database 16 is a mass storage device that stores a plurality of background-endoscopic images serving as the background of a foreground image. The background-endoscopic images are, for example, endoscopic images that are picked up by an endoscope system 100 (see FIG. 13). The background-endoscopic images may be endoscopic images that are picked up by a plurality of different endoscope apparatuses (not shown). It is preferable that the background-endoscopic images are images where a treatment tool does not appear. The background-endoscopic image database 16 may store information about whether or not a lesion (an example of a region of interest) is present in images, information about the positions of lesions, and information about the classifications of lesions in association with the background-endoscopic images as necessary. The information about the positions of lesions may be information about the coordinates of lesions in images, or may be information about rectangles surrounding lesions or information about data of mask hiding lesions.

A lesion is not limited to a region caused by a disease, and includes a region that is in a state different from a state where the appearance is normal. Examples of a lesion include a polyp, a cancer, the colonic diverticula, an inflammation, a treatment scar, such as an endoscopic mucosal resection (EMR) scar or an endoscopic submucosal dissection (ESD) scar, a clipped portion, a bleeding point, a perforation, blood vessel heteromorphism, and the like. Examples of the classification of a lesion include two classifications of tumor and non-tumor, the NICE classification, and the like.

The learning-endoscopic image database 18 is a mass storage device that stores learning-endoscopic images. The learning-endoscopic images are endoscopic images that are picked up by the endoscope system 100 (see FIG. 13). The learning-endoscopic images may be endoscopic images that are picked up by a plurality of different endoscope apparatuses (not shown). The learning-endoscopic images include images where a treatment tool appears and images where a treatment tool does not appear. The learning-endoscopic image database 18 may store information about whether or not a treatment tool is present in images, information about whether or not a lesion is present in images, information about the positions of lesions, and information about the classifications of lesions in association with the learning-endoscopic images as necessary.

At least two of the foreground-material image database 14, the background-endoscopic image database 16, and the learning-endoscopic image database 18 may be the same storage devices. Further, at least one of the foreground-material image database 14, the background-endoscopic image database 16, or the learning-endoscopic image database 18 may be provided outside the endoscopic image learning device 10. In this case, images are acquired from an external database through the communication unit 12.

The operation unit 20 is an input interface that receives various operations to be input to the endoscopic image learning device 10. A keyboard, a mouse, or the like, which is connected to a computer by wire or radio, is used as the operation unit 20.

The CPU 22 reads various programs stored in a ROM 26, a hard disk drive (not shown), or the like, and performs various kinds of processing. The RAM 24 is used as a work area for the CPU 22. Further, the RAM 24 is used as a storage unit that temporarily stores the read programs and various data. The endoscopic image learning device 10 may comprise a graphics processing unit (GPU).

The display unit 28 is an output interface on which necessary information of the endoscopic image learning device 10 is displayed. Various monitors, such as an LCD monitor that can be connected to a computer, are used as the display unit 28.

The CPU 22 of the endoscopic image learning device 10 reads an endoscopic image learning program, which is stored in the ROM 26, the hard disk drive, or the like, according to an instruction input from the operation unit 20 and executes the endoscopic image learning program. Accordingly, an endoscopic image learning method to be described later is performed, so that superimposed images are generated and a learning model is learned using the superimposed images.

The endoscopic image learning program, which causes a computer to perform the endoscopic image learning method, may be provided in a state where the endoscopic image learning program is stored in a computer-readable non-temporary recording medium.

An example where the endoscopic image learning device 10 is formed of a single personal computer or a single workstation has been described here, but the endoscopic image learning device 10 may be formed of a plurality of personal computers. For example, a personal computer generating superimposed images and a personal computer performing machine learning can be separated from each other, so that the generation of learning data and the generation of a learning model can be performed without being physically and temporally restricted mutually.

First Embodiment

A learning model for performing the image recognition of whether or not a treatment tool is present in an endoscopic image is generated in a first embodiment.

Endoscopic Image Learning Device

Figure 4:
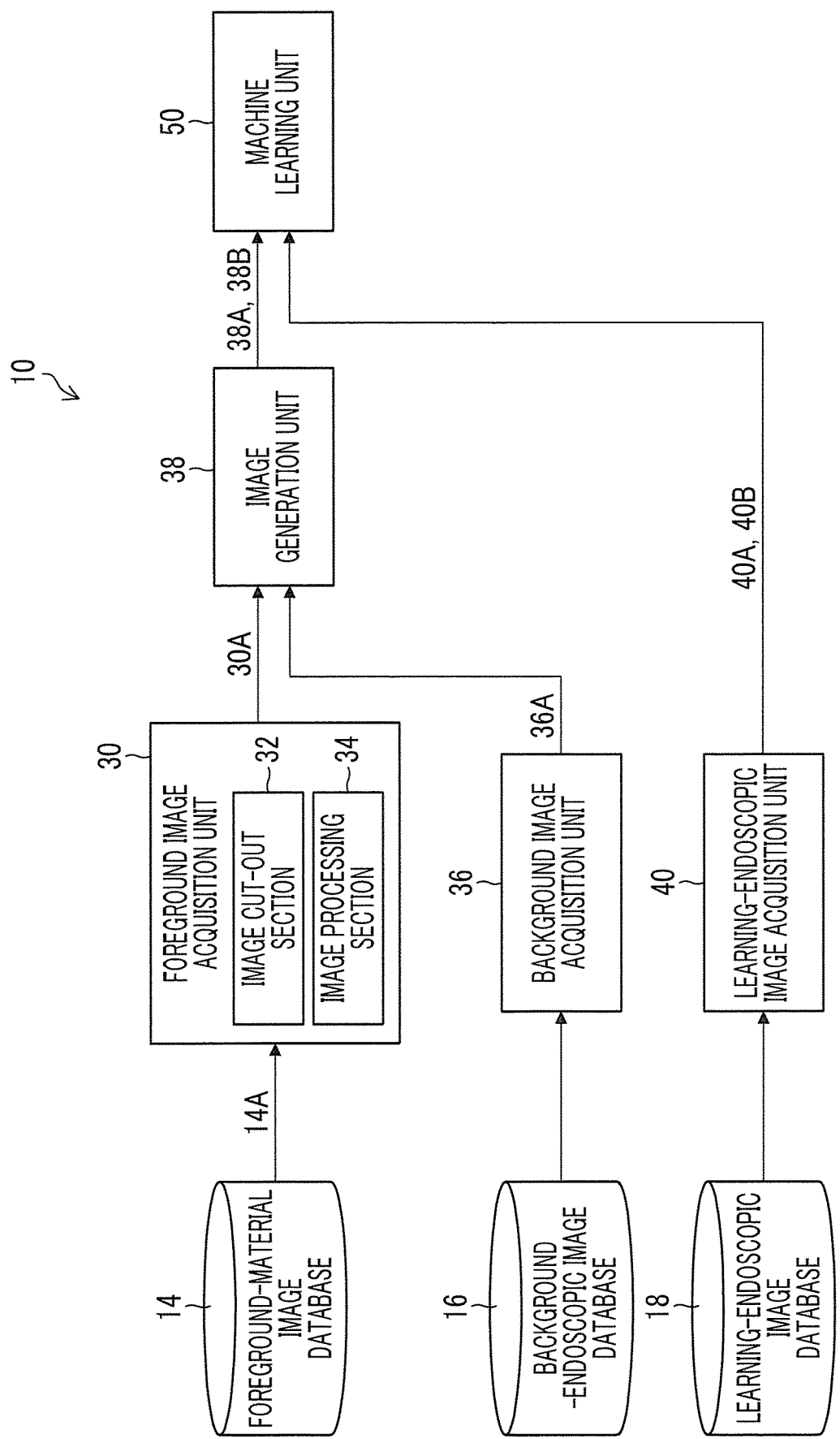
FIG. 4 is a functional block diagram showing the main functions of an endoscopic image learning device 10 according to a first embodiment.

FIG. 4 is a functional block diagram showing the main functions of an endoscopic image learning device 10 according to a first embodiment. The endoscopic image learning device 10 comprises a foreground image acquisition unit 30, a background image acquisition unit 36, an image generation unit 38, a learning-endoscopic image acquisition unit 40, and a machine learning unit 50.

The foreground image acquisition unit 30 acquires a foreground image 30A in which a treatment tool is extracted. Here, the foreground image acquisition unit 30 acquires a foreground image 30A in which a treatment tool is extracted from a foreground-material image 14A. The foreground image acquisition unit 30 comprises an image cut-out section 32 and an image processing section 34.

The image cut-out section 32 (an example of a foreground-material image acquisition section) acquires a foreground-material image 14A from the foreground-material image database 14. The image cut-out section 32 cuts out (an example of extraction) a region where a treatment tool appears from the acquired foreground-material image 14A. The cut-out region is the foreground image 30A.

The image processing section 34 acquires the foreground image 30A from the image cut-out section 32. The image processing section 34 performs specific processing on the acquired foreground image 30A. The specific processing is at least one image processing of affine transformation processing, color conversion processing, or noise application processing.

The image processing section 34 can correct a difference between an optical system of an endoscope apparatus and an optical system, which picks up the foreground image 30A, such as a focal length, by performing affine transformation processing on the foreground image 30A. That is, the foreground image 30A having been subjected to affine transformation processing has the same characteristics as an image that is picked up by the optical system of the endoscope apparatus.

The image processing section 34 can correct a difference in color between the foreground image 30A and a background-endoscopic image 36A to be described later by performing color conversion processing on the foreground image 30A. For example, the image processing section 34 can reproduce the reflection of a mucous membrane of the background-endoscopic image 36A in the foreground image 30A by color conversion processing.

The image processing section 34 can correct the amount of noise by performing noise application processing on the foreground image 30A. For example, in a case where a background-endoscopic image 36A to be described later is a dark image and includes a lot of noise, the image processing section 34 can reproduce the same darkness as the background-endoscopic image 36A by applying the same noise as the background-endoscopic image 36A to the foreground image 30A.

The foreground image 30A, which has been subjected to specific processing by the image processing section 34, is input to the image generation unit 38.

The background image acquisition unit 36 acquires the background-endoscopic image 36A, which serves as the background of a foreground image, from the background-endoscopic image database 16.

The image generation unit 38 acquires the foreground image 30A from the foreground image acquisition unit 30. Further, the image generation unit 38 acquires the background-endoscopic image 36A from the background image acquisition unit 36. The image generation unit 38 generates a superimposed image 38A where the foreground image 30A is superimposed on the background-endoscopic image 36A. Furthermore, the image generation unit 38 generates correct answer data 38B of the generated superimposed image 38A.

Here, the image generation unit 38 acquires a plurality of different background-endoscopic images 36A with regard to at least one foreground image 30A, and generates a plurality of superimposed images 38A on which the foreground image is superimposed. It is preferable that combinations of the foreground image 30A and the background-endoscopic images 36A are determined randomly. Further, all the correct answer data 38B of the generated superimposed images 38A correspond to "with a treatment tool". The image generation unit 38 outputs as many data sets of the superimposed images 38A and the correct answer data 38B as the number of the generated superimposed images 38A.

The learning-endoscopic image database 18 according to this embodiment stores information about whether or not a treatment tool is present in images in association with the learning-endoscopic images. The learning-endoscopic image acquisition unit 40 acquires a learning-endoscopic image 40A from the learning-endoscopic image database 18. Further, the learning-endoscopic image acquisition unit 40 acquires correct answer data 40B from the information about whether or a treatment tool is present that is associated with the acquired learning-endoscopic image 40A. The correct answer data 40B corresponds to "with a treatment tool" and "with no treatment tool" depending on the learning-endoscopic image 40A. The learning-endoscopic image acquisition unit 40 inputs a data set of the acquired learning-endoscopic image 40A and the acquired correct answer data 40B to the machine learning unit 50.

The machine learning unit 50 performs the learning of a learning model for image recognition using at least the superimposed image 38A. Here, the machine learning unit 50 generates a learning model for image recognition using the superimposed image 38A and the learning-endoscopic image 40A. The machine learning unit 50 builds a convolutional neural network (CNN) that is one of learning models.

Figure 5:
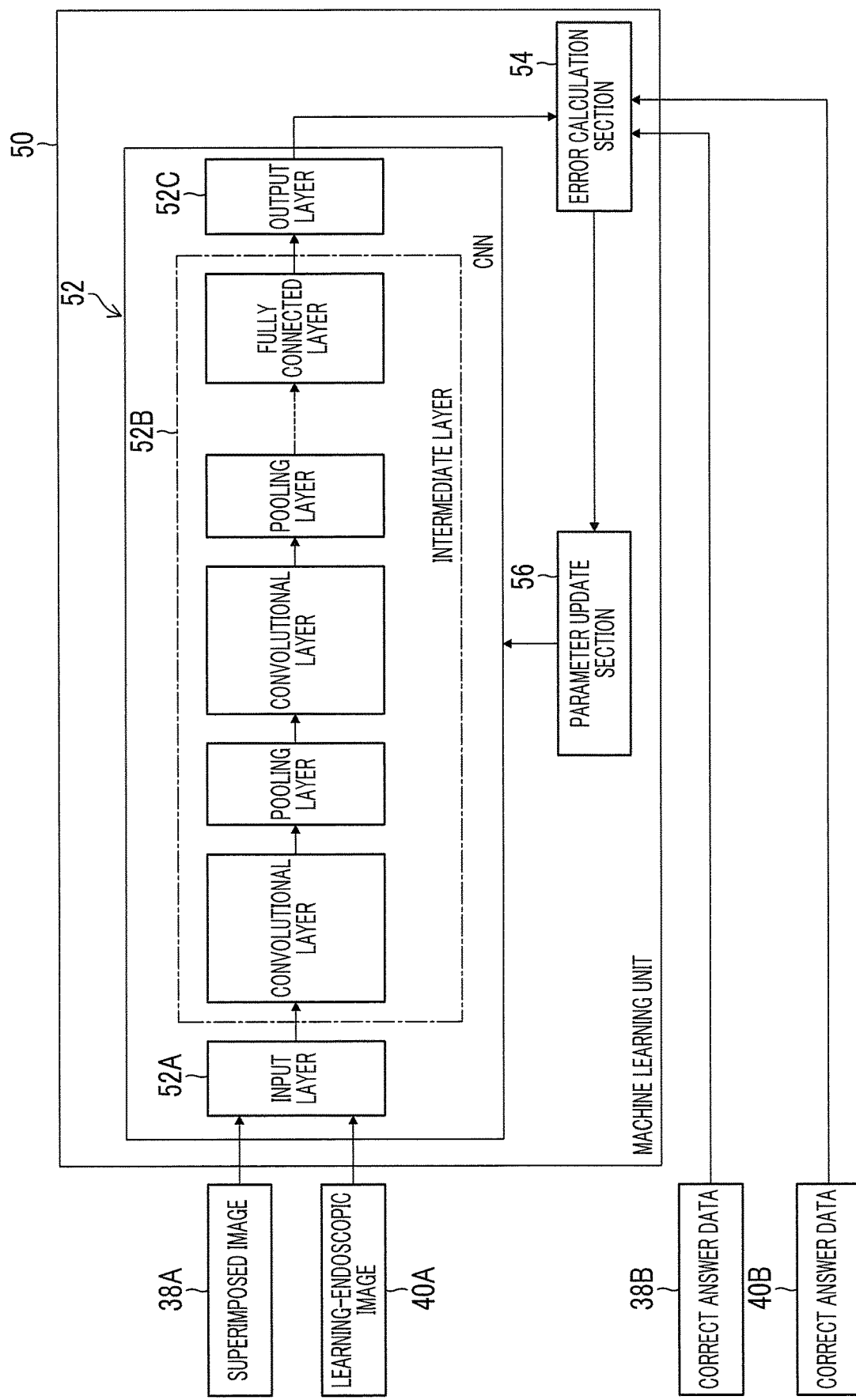
FIG. 5 is a functional block diagram showing the main functions of a machine learning unit 50.

FIG. 5 is a functional block diagram showing the main functions of the machine learning unit 50. The machine learning unit 50 comprises a CNN 52, an error calculation section 54, and a parameter update section 56.

The CNN 52 is a recognizer that performs the image recognition of whether or not a treatment tool is present in the endoscopic image. The CNN 52 has multi-layer structure, and includes a plurality of weight parameters. The CNN 52 is changed to a model having learned from a model not yet learned in a case where the weight parameters are updated to optimum values from initial values.

The CNN 52 comprises an input layer 52A, an intermediate layer 52B, and an output layer 52C. Each of the input layer 52A, the intermediate layer 52B, and the output layer 52C has structure where a plurality of "nodes" are connected by "edges".

The superimposed image 38A and the learning-endoscopic image 40A, which are objects to be learned, are input to the input layer 52A.

The intermediate layer 52B is a layer that extracts features from an image input from the input layer. The intermediate layer 52B includes a plurality of sets and a fully connected layer, and each of the sets is formed of a convolutional layer and a pooling layer. The convolutional layer acquires a feature map by performing convolution operation, which uses filters, on nodes close to a previous layer. The pooling layer reduces a feature map, which is output from the convolutional layer, to obtain a new feature map. The fully connected layer connects all the nodes of the previous layer (here, the pooling layer). The convolutional layer functions to perform feature extraction, such as edge extraction, from an image, and the pooling layer functions to give robustness so that the extracted features are not affected by translation and the like. The intermediate layer 52B is not limited to a case where one set is formed of the convolutional layer and the pooling layer. The intermediate layer 52B also includes a case where the convolutional layers are successive, and a normalization layer.

The output layer 52C is a layer that outputs the result of recognition of whether or not a treatment tool is present in the endoscopic image on the basis of the features extracted by the intermediate layer 52B.

In a case where the CNN 52 having learned classifies whether or not a treatment tool is present in the endoscopic image, for example, endoscopic images are classified into two categories of "with a treatment tool" and "with no treatment tool" and the result of recognition is output as two scores corresponding to "with a treatment tool" and "with no treatment tool". The sum of the two scores is 100%.

Any initial value of the number of filters applied to each convolutional layer of the CNN 52 not yet learned, an offset value, and the weight of connection of the fully connected layer to the next layer are set.

The error calculation section 54 acquires the result of recognition output from the output layer 52C of the CNN 52 and correct answer data corresponding to the input image, and calculates an error therebetween. For example, softmax cross entropy, mean squared error (MSE), or the like is considered as a method of calculating an error.

The parameter update section 56 adjusts the weight parameters of the CNN 52 by an error backpropagation method on the basis of the error calculated by the error calculation section 54.

This processing for adjusting the parameters is repeatedly performed, and repeated learning is performed until a difference between the output of the CNN 52 and the correct answer data is reduced.

The machine learning unit 50 optimizes each parameter of the CNN 52 using at least the data set of the superimposed image 38A and the correct answer data 38B. Here, the machine learning unit 50 optimizes each parameter of the CNN 52 using the data set of the superimposed image 38A and the correct answer data 38B and the data set of the learning-endoscopic image 40A and the correct answer data 40B. Learning may be performed in a state where the data sets are mixed. A mini-batch method including extracting a predetermined number of data sets, performing batch processing of learning using the extracted data sets, and repeating this may be used for the learning of the machine learning unit 50.

The machine learning unit 50 may not use correct answer data depending on recognition processing that is required to be realized. Further, the machine learning unit 50 may extract features by an algorithm, which is designed in advance, such as edge extraction, and may learn with a support vector machine or the like using the information about the features.

Endoscopic Image Learning Method

Figure 6:
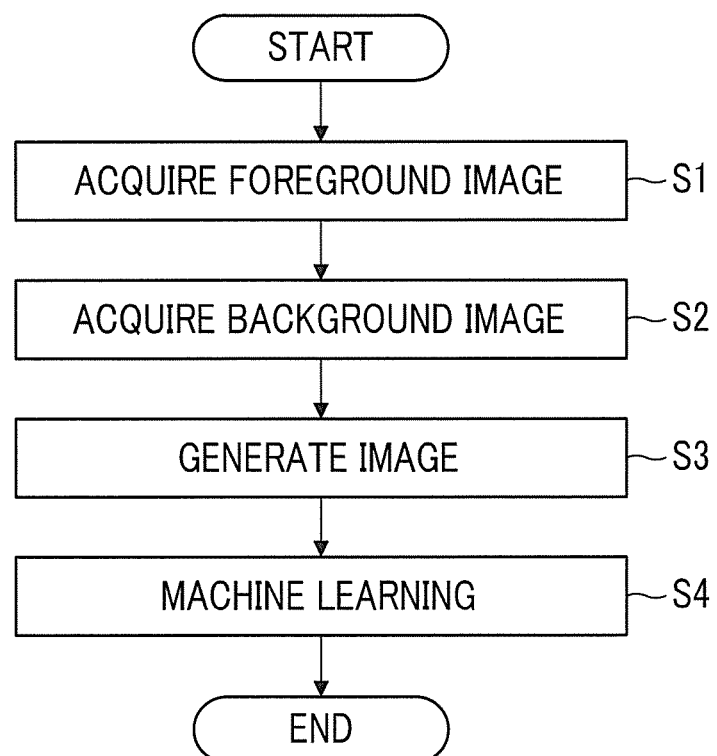
FIG. 6 is a flowchart showing an example of an endoscopic image learning method to be performed by the endoscopic image learning device 10.

FIG. 6 is a flowchart showing an example of an endoscopic image learning method to be performed by the endoscopic image learning device 10. The endoscopic image learning method includes a foreground image acquisition step (Step S1), a background image acquisition step (Step S2), an image generation step (Step S3), and a machine learning step (Step S4).

In Step S1, the foreground image acquisition unit 30 acquires the foreground image 30A in which a treatment tool is extracted. That is, the image cut-out section 32 of the foreground image acquisition unit 30 acquires the foreground-material image 14A from the foreground-material image database 14 and cuts out a region where a treatment tool appears to generate the foreground image 30A.

Figure 7:
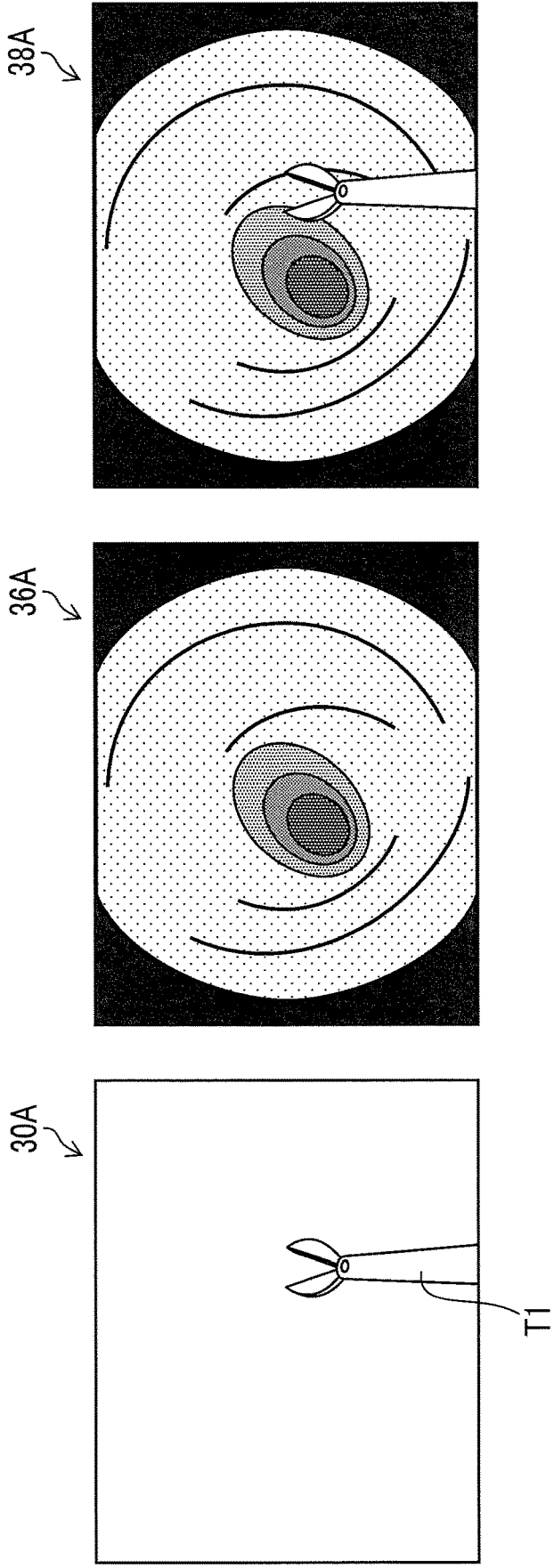
FIG. 7 is a diagram illustrating the image processing of the endoscopic image learning device 10.

FIG. 7 is a diagram illustrating the image processing of the endoscopic image learning device 10. Here, the image cut-out section 32 acquires the foreground-material image 14A shown in FIG. 2 as an example. FIG. 7 shows an example of the foreground image 30A that is cut out from the foreground-material image 14A by the image cut-out section 32. As shown in FIG. 7, the foreground image 30A is an image of which a region except for the region of a treatment tool T1 is transparent. The foreground image 30A may be an image of only the region of the treatment tool T1.

Returning to FIG. 6, in Step S2, the background image acquisition unit 36 acquires the background-endoscopic image 36A, which serves as the background of a foreground image, from the background-endoscopic image database 16. FIG. 7 shows an example of the background-endoscopic image 36A that is acquired by the background image acquisition unit 36. As shown in FIG. 7, the background-endoscopic image 36A is an image where a treatment tool does not appear.

In Step S3, the image generation unit 38 generates the superimposed image 38A where the foreground image 30A is superimposed on the background-endoscopic image 36A. FIG. 7 shows an example of the superimposed image 38A where the foreground image is superimposed by the image generation unit 38. As shown in FIG. 7, the superimposed image 38A is the same image as the endoscopic image that is picked up during the use of a treatment tool.

In Step S4, the machine learning unit 50 performs the learning of a learning model for image recognition. Here, the machine learning unit 50 generates a learning model for image recognition using the superimposed image and the learning-endoscopic image.

The data sets of a plurality of superimposed images 38A, which are generated in a case where the processing of Steps S1 to S3 are performed in advance, and the correct answer data 38B may be stored in a database (not shown), and the machine learning unit 50 may read a plurality of data sets from the database to perform the processing of Step S4.

An endoscopic image, which is to be observed using an endoscope, is changed depending on a change in viewpoint or a change in the shape of a tube. However, in a state where a positional relationship between an object and an image pickup system of an endoscope is not changed, the position of the object in an image is not changed. For example, a treatment tool protruding from the forceps outlet 105 (see FIG. 14) provided at the distal end part of the endoscope is always seen basically in the same manner. The same applies to the cap 102F (see FIG. 13) that is mounted on the distal end part of the endoscope. That is, a state where a normal endoscopic image of a living body is the background and a treatment tool is the foreground is made.

According to this embodiment, since a superimposed image where the foreground image of a treatment tool is combined with on an endoscopic image serving as a background image is generated and is used as learning data, learning data can be padded. Accordingly, the performance of recognition of an endoscopic image including a treatment tool can be improved.

According to this embodiment, it is possible to perform learning without collecting a large number of endoscopic images that include a treatment tool of which data is not easily collected. Further, since an endoscopic image to be obtained during the use of a treatment tool is reproduced artificially, learning for causing the endoscope to normally operate even at the time of detection of a lesion and the like can be performed.

A method of automatically and significantly padding the amount of learning data by combining a foreground image with a background image is considered even in the recognition of a general image. However, since images having a sense of incongruity are often obtained in most cases, there is less contribution to the improvement of accuracy even though learning is performed using these images. Further, since time is required to generate composite images in a case where images not having a sense of incongruity are to be generated, it is difficult to achieve the mass production of the images not having a sense of incongruity.

On the other hand, in the recognition of an endoscopic image, a treatment tool is an artifact positioned in the foreground and is an object "having a sense of incongruity" with respect to a living body serving as the background. Accordingly, the improvement of accuracy can be expected even in the learning using learning images that are obtained through the automatic and mass production of composite images.

Another Aspect of Foreground Image

In the above-mentioned example, the foreground-material images 14A stored in the foreground-material image database 14 are images that are picked up in a case where a treatment tool is used while a living body is observed using an endoscope. For this reason, the foreground image acquisition unit 30 can acquire a more realistic foreground image 30A in which the state of a living body, such as the lumen, appears on a portion reflecting light, such as a metal portion of a treatment tool.

An example where an image, which is picked up in a case where a treatment tool is used while a portion other than a living body is observed using an endoscope, is used as the foreground-material image 14A will be described here.

In this case, the sense of reality of the foreground image 30A is lower than that in the first embodiment. However, since a treatment tool does not need to be actually used in a living body, there is a merit that the foreground-material image 14A is easily collected.

Figure 8:
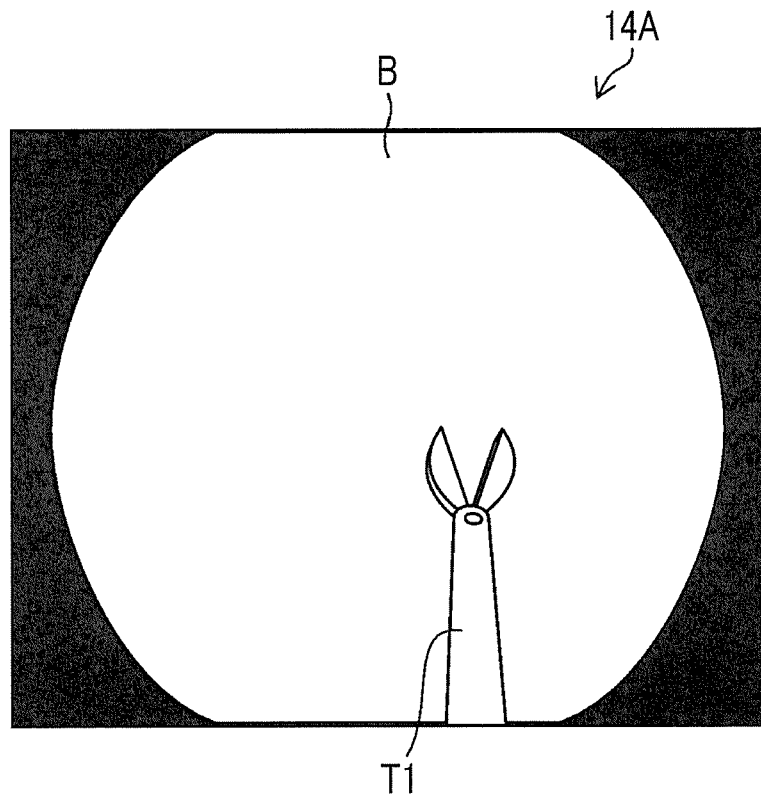
FIG. 8 is a diagram showing an example of the foreground-material image 14A.

FIG. 8 is a diagram showing an example of the foreground-material image 14A. A background B of a treatment tool T1 has a uniform color in the foreground-material image 14A. In a case where an image is picked up so that the region of the background has a uniform color as described above, a foreground image 30A can also be mechanically cut out by a method "of cutting out a portion, which has a hue out of a predetermined range, of the foreground-material image 14A as the foreground image 30A".

Further, a foreground image 30A may be cut out from an image picked up by an image pickup device other than an image pickup system of an endoscope, that is, an image other than an endoscopic image. This image is different from the image of a treatment tool picked up by an image pickup system of an endoscope, but the foreground-material image 14A can be more easily collected and the foreground image 30A can be more easily generated.

The foreground image 30A may be used just as it is, but may be subjected to various kinds of conversion by the image processing section 34 to increase the variations of the foreground image 30A.

Figure 9:
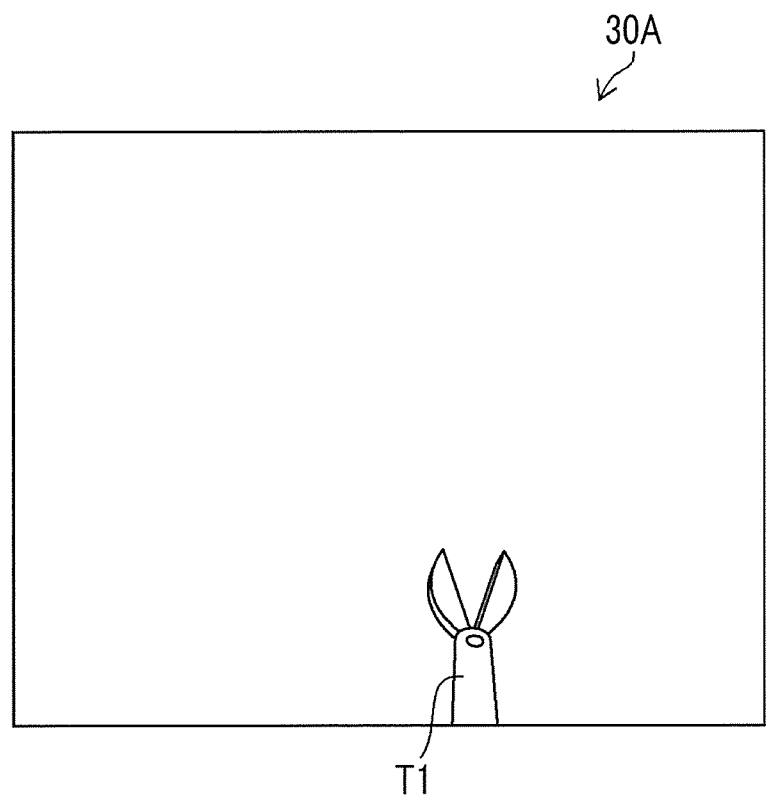
FIG. 9 is a diagram showing a foreground image 30A that is converted from a foreground image 30A shown in FIG. 7.
Figure 10:
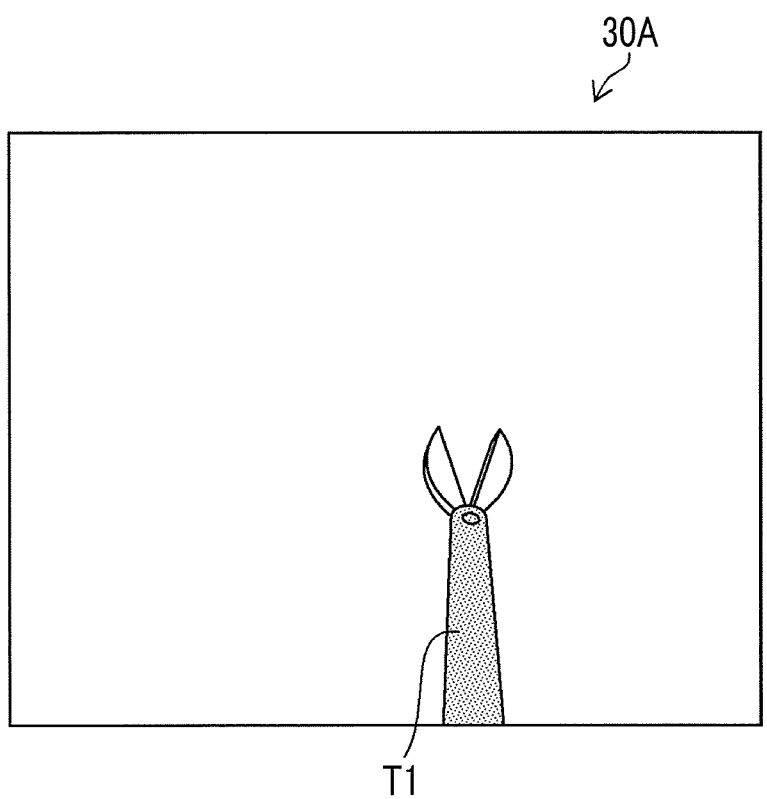
FIG. 10 is a diagram showing a foreground image 30A that is converted from the foreground image 30A shown in FIG. 7.

FIGS. 9 and 10 are diagrams showing foreground images 30A that are converted from the foreground image 30A shown in FIG. 7. The foreground image 30A shown in FIG. 9 is an image where the treatment tool T1 of foreground image 30A of FIG. 7 is translated downward in FIG. 7. A change in the insertion length of the treatment tool can be reproduced in a case where such a foreground image 30A is used. Further, the foreground image 30A shown in FIG. 10 is an image where the color tone of a cylindrical portion (sheath portion) of the treatment tool T1 of FIG. 7 is changed. The use of treatment tools, which have the same shape and different colors, can be reproduced in a case where such a foreground image 30A is used. For example, the learning data of a treatment tool T1 including a sheath portion having a color similar to the color of the mucous membrane of a living body can be generated.

Another Aspect of Background Image

It is preferable that the background-endoscopic images 36A stored in the background-endoscopic image database 16 are the picked-up images of a living body. Among them, an image where a foreground appears, such as an image picked up during the use of a treatment tool or an image blurred due to the adhesion of water to an image pickup system during the supply of water, is not suitable as the background to be superimposed. For this reason, such an image is not used. Further, since a treatment tool is rarely used in a case where an observation is made at a position close to body tissue, it is preferable that a close-up image is excluded.

Another Aspect of Learning Model

In this embodiment, the machine learning unit 50 generates a learning model for performing the image recognition of whether or not a treatment tool is present in an endoscopic image. However, other variations of the learning model are considered in the image recognition. For example, the learning model may be a learning model for performing the image recognition of the type of a treatment tool present in an endoscopic image.

In this case, the label of the class of a treatment tool of the foreground image 30A is given as the correct answer data 38B of the superimposed image 38A. The label of the class of a treatment tool may be stored in the foreground-material image database 14 in association with the foreground-material image 14A.

Further, the learning model may be a learning model for performing the segmentation of a treatment tool that distinguishes the region of a treatment tool from a region other than the region of a treatment tool.

FIG. 11 is a diagram showing a superimposed image 38A and correct answer data 38B of the superimposed image 38A in the case of a learning model for recognizing the segmentation of a treatment tool. As shown in FIG. 11, a treatment tool T1 is superimposed on the superimposed image 38A. Further, the correct answer data 38B is a region M1 corresponding to the region of the treatment tool T1. Here, the correct answer data 38B corresponds to an image of which a region other than the region M1 is masked.

The learning model may not be the recognition of a treatment tool. For example, the learning model may be a learning model for performing the classification of a lesion (an example of the classification of an image). Even though a foreground image is superimposed, the diagnosis result of a lesion appearing in the background image is not changed. Accordingly, these superimposed images can be used for learning. Further, a risk that the use of a treatment tool affects the result of classification other than assumption can be reduced by padding. In this case, a label related to a lesion given to a background image 16A may not be changed and learning may be performed using the label as correct answer data.

The learning model may be a learning model for recognizing the position of a lesion. In this case, the area of a lesion of the background image 16A may be changed due to the combination of the foreground image 30A. In this case, correct answer data is changed as described below.

Figure 12:
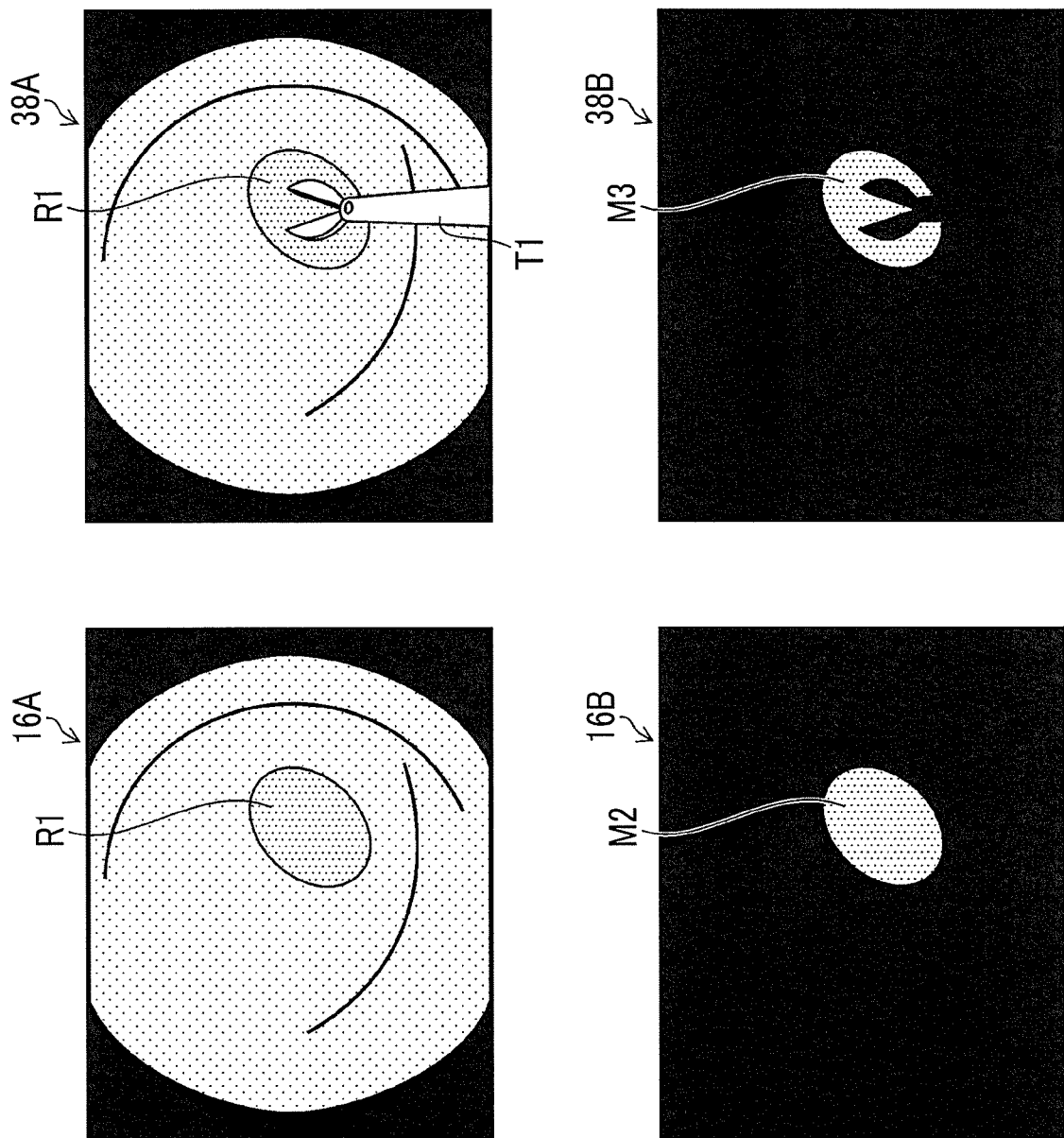
FIG. 12 is a diagram showing examples of a background image 16A, correct answer data 16B of the background image 16A, a superimposed image 38A generated from the background image 16A, and correct answer data 38B of the superimposed image 38A in the case of a learning model for recognizing the position of a lesion.

FIG. 12 is a diagram showing examples of a background image 16A, correct answer data 16B of the background image 16A, a superimposed image 38A generated from the background image 16A, and correct answer data 38B of the superimposed image 38A in the case of a learning model for recognizing the position of a lesion.

As shown in FIG. 12, a region R1 of interest corresponding to a lesion is present in the background image 16A. Further, the correct answer data 16B of the background image 16A is a region M2 corresponding to the region R1 of interest.

Furthermore, a treatment tool T1 is superimposed on the superimposed image 38A, and the treatment tool T1 overlaps with a part of the region R1 of interest. Accordingly, the correct answer data 38B in this case is a region M3 of a difference between the region M2 and the region of the treatment tool T1 as shown in FIG. 12. Since the machine learning unit 50 performs learning using the correct answer data 38B, the machine learning unit 50 can appropriately learn a learning model for recognizing the position of a lesion.

Second Embodiment

An example of an endoscope system to which the endoscopic image learning device 10 is applied will be described.

Configuration of Endoscope System

Figure 13:
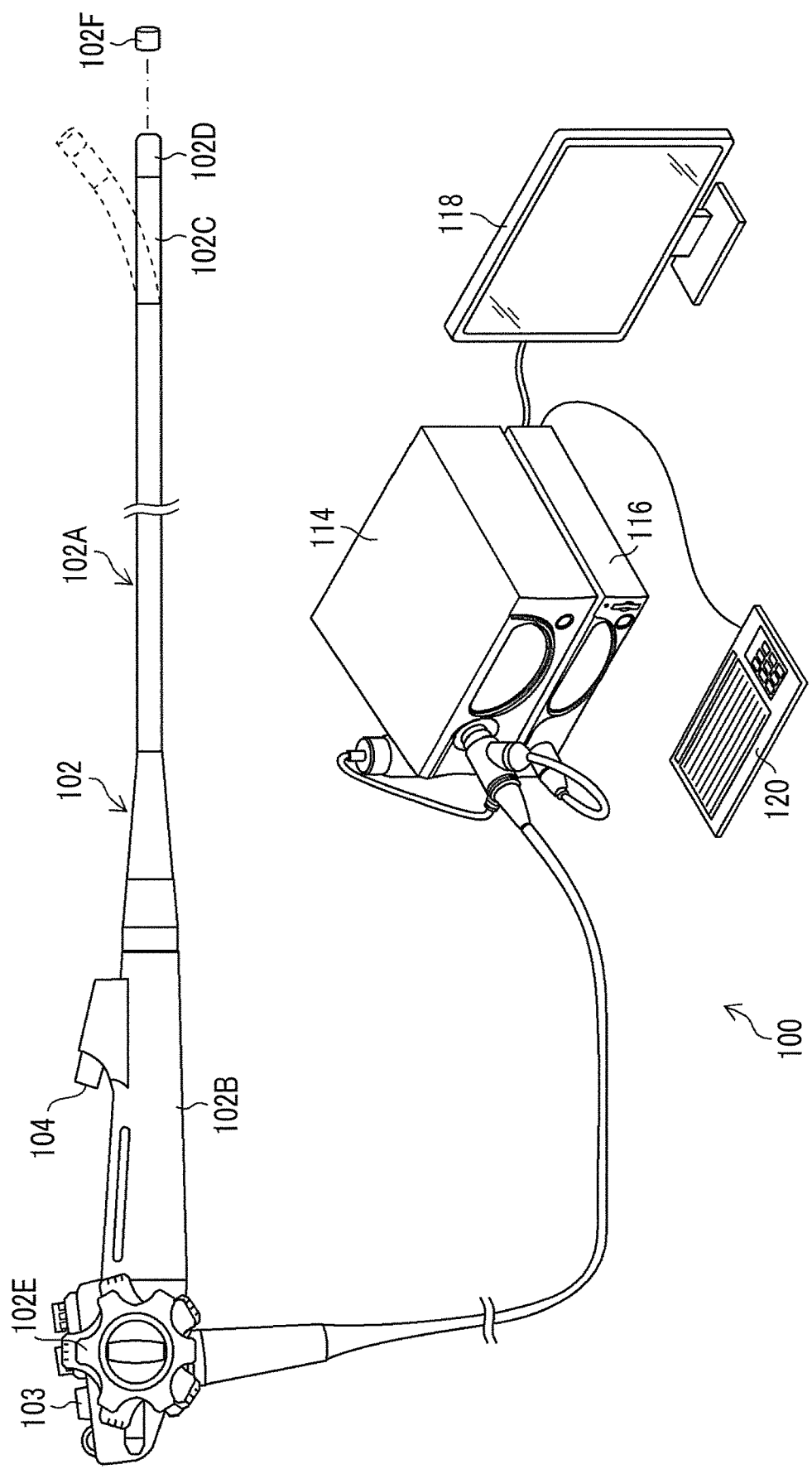
FIG. 13 is a diagram showing the appearance of an endoscope system 100 according to a second embodiment.

FIG. 13 is a diagram showing the appearance of an endoscope system 100 according to a second embodiment. As shown in FIG. 13, the endoscope system 100 comprises an endoscope 102, a light source device 114, a processor device 116, a display unit 118, and an input unit 120.

The endoscope 102 is a lower endoscope that is inserted from the anus of an examinee and is used to observe the rectum, the large intestine, and the like. The endoscope 102 is optically connected to the light source device 114. Further, the endoscope 102 is electrically connected to the processor device 116.

The endoscope 102 includes an insertion part 102A that is to be inserted into the body cavity of an examinee, an operation part 102B that is provided at the proximal end portion of the insertion part 102A, and a bendable part 102C and a distal end part 102D that are provided on the distal end side of the insertion part 102A.

The operation part 102B is provided with angle knobs 102E and a mode changeover switch 103.

The bendable part 102C operates to be bent by the operation of the angle knobs 102E. The distal end part 102D is made to face in a desired direction by the bending operation of the bendable part 102C.

The mode changeover switch 103 is used for an operation for switching an observation mode. The endoscope system 100 has a plurality of observation modes of which the wavelength patterns of irradiation light are different from each other. A doctor can set the endoscope system 100 to a desired observation mode by operating the mode changeover switch 103. The endoscope system 100 generates an image corresponding to a set observation mode by a combination of a wavelength pattern and image processing, and displays the image on the display unit 118.

Further, the operation part 102B is provided with an acquisition instruction input part (not shown). The acquisition instruction input part is an interface that is used by a doctor to input an instruction to acquire a static image. The acquisition instruction input part receives an instruction to acquire a static image. The instruction to acquire a static image, which is received by the acquisition instruction input part, is input to the processor device 116.

A forceps port 104 is provided on the distal end side of the operation part 102B. A treatment tool is inserted into the forceps port 104. The forceps port 104 communicates with the forceps outlet 105 (see FIG. 14) of the distal end part 102D of the insertion part 102A through a forceps channel (not shown) provided in the insertion part 102A.

Figure 14:
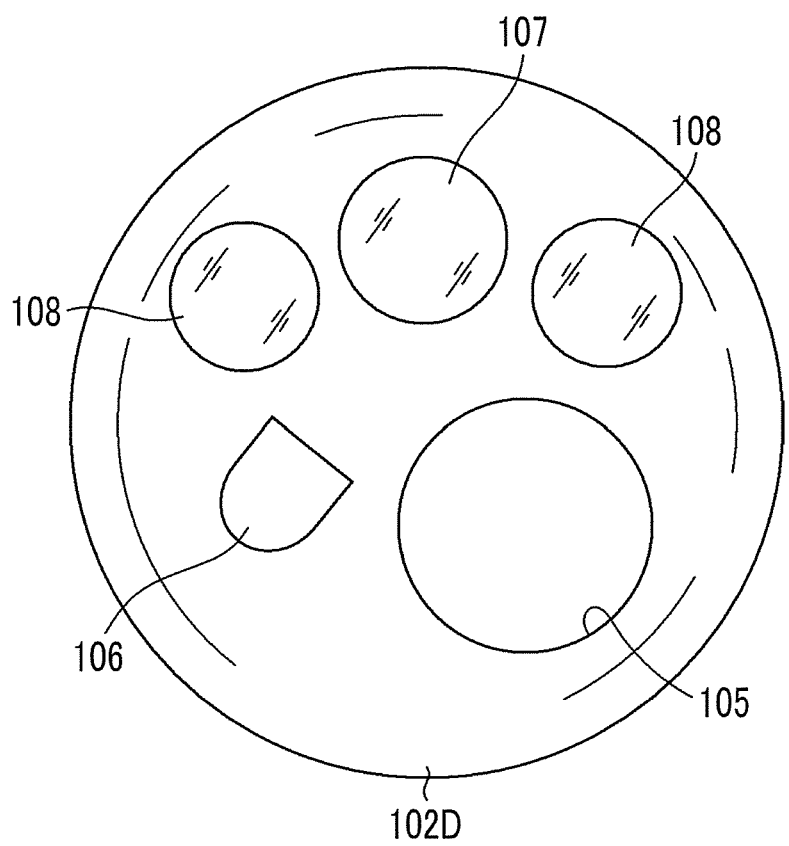
FIG. 14 is a front view of a distal end part 102D of an insertion part 102A.

FIG. 14 is a front view of the distal end part 102D of the insertion part 102A. As shown in FIG. 14, the distal end part 102D is provided with a forceps outlet 105 through the treatment tool inserted from the forceps port 104 protrudes, an air/water supply nozzle 106 that ejects air or water, an observation window 107 that guides reflected light of irradiation light L0 (see FIG. 15) to an image pickup unit 137 (see FIG. 15), and illumination windows 108 through which an image pickup object is irradiated with the irradiation light L0.

There is a case where a cap 102F (an example of a treatment tool for an endoscope) is mounted on the distal end part 102D as shown in FIG. 13. The cap 102F is used to keep a constant distance between an image pickup object and the observation window 107 in a state where the cap 102F is in contact with the image pickup object.

The processor device 116 is electrically connected to the display unit 118 and the input unit 120. The display unit 118 is a display device that outputs and displays an image to be observed, information related to the image to be observed, and the like. The input unit 120 functions as a user interface that receives input operations, such as the function settings of the endoscope system 100 and various instructions.

Figure 15:
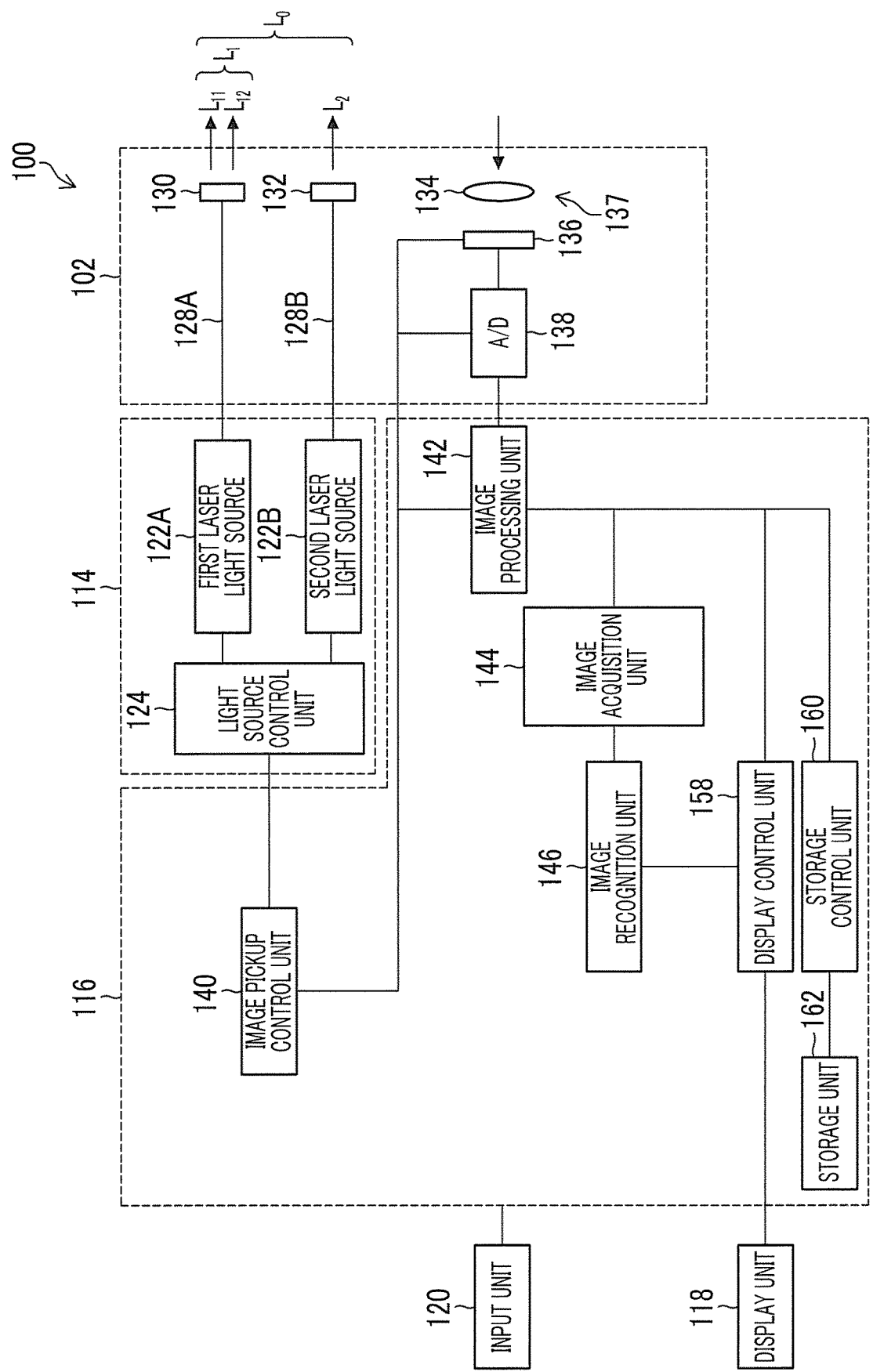
FIG. 15 is a block diagram showing the functions of the endoscope system 100.

FIG. 15 is a block diagram showing the functions of the endoscope system 100. As shown in FIG. 15, the light source device 114 comprises a first laser light source 122A, a second laser light source 122B, and a light source control unit 124.

The first laser light source 122A is a blue laser light source having a central wavelength of 445 nm. The second laser light source 122B is a violet laser light source having a central wavelength of 405 nm. A laser diode can be used as each of the first laser light source 122A and the second laser light source 122B. The light emission of the first laser light source 122A and the light emission of the second laser light source 122B are individually controlled by the light source control unit 124. A ratio of the light emission intensity of the first laser light source 122A to the light emission intensity of the second laser light source 122B is adapted to be changeable.

Further, as shown in FIG. 15, the endoscope 102 comprises an optical fiber 128A, an optical fiber 128B, a fluorescent body 130, a diffusion member 132, an image pickup lens 134, an image pickup element 136, and an analog/digital conversion unit 138.

The fluorescent body 130 disposed in the distal end part 102D of the endoscope 102 is irradiated with laser light, which is emitted from the first laser light source 122A, by the optical fiber 128A. The fluorescent body 130 includes plural kinds of fluorescent bodies that absorb a part of blue laser light from the first laser light source 122A and are excited to emit green to yellow light. Accordingly, green to yellow excitation light L11, which are generated using blue laser light emitted from the first laser light source 122A as excitation light, and blue laser light L12, which is transmitted through the fluorescent body 130 without being absorbed by the fluorescent body 130, are mixed to each other, so that light emitted from the fluorescent body 130 becomes white (pseudo white) light L1.

White light mentioned here is not limited to light that strictly includes all wavelength components of visible light. For example, white light may be light that includes light having specific wavelength ranges, such as R light, G light, and B light; and may be light that also includes light including wavelength components of green to red light, light including wavelength components of blue to green light, or the like in a broad sense.

On the other hand, the diffusion member 132 disposed in the distal end part 102D of the endoscope 102 is irradiated with laser light, which is emitted from the second laser light source 122B, by the optical fiber 128B. A resin material having translucency and the like can be used for the diffusion member 132. Light emitted from the diffusion member 132 is light L2 of which the amount is uniformized in an irradiated region and which has a narrow wavelength range.

FIG. 16 is a graph showing the intensity distribution of light L1 and light L2. The light source control unit 124 changes a ratio of the amount of light emitted from the first laser light source 122A to the amount of light emitted from the second laser light source 122B. Accordingly, a ratio of the amount of light L1 to the amount of light L2 s changed, so that the wavelength pattern of irradiation light L0, which is composite light of light L1 and light L2, is changed. Therefore, irradiation light L0 of which the wavelength pattern varies depending on an observation mode can be applied.

Returning to the description of FIG. 15, the image pickup lens 134, the image pickup element 136, and the analog/digital conversion unit 138 form an image pickup unit 137. The image pickup unit 137 is disposed in the distal end part 102D of the endoscope 102.

The image pickup lens 134 causes incident light to form an image on the image pickup element 136. The image pickup element 136 generates analog signals corresponding to received light. A charge coupled device (CCD) image sensor or a complementary metal oxide semiconductor (CMOS) image sensor is used as the image pickup element 136. Analog signals output from the image pickup element 136 are converted into digital signals by the analog/digital conversion unit 138, and the digital signals are input to the processor device 116.

Further, the processor device 116 comprises an image pickup control unit 140, an image processing unit 142, an image acquisition unit 144, and an image recognition unit 146.

The image pickup control unit 140 controls the light source control unit 124 of the light source device 114, the image pickup element 136 and the analog/digital conversion unit 138 of the endoscope 102, and the image processing unit 142 of the processor device 116 to control the taking of a video and a static image performed by the endoscope system 100 overall.

The image processing unit 142 performs image processing on the digital signals input from the analog/digital conversion unit 138 of the endoscope 102, and generates image data representing an image (hereinafter, referred to as an image). The image processing unit 142 performs image processing corresponding to the wavelength pattern of irradiation light at the time of image pickup.

The image acquisition unit 144 acquires the image that is generated by the image processing unit 142. That is, the image acquisition unit 144 sequentially acquires a plurality of images of the inside of a living body of an examinee that are picked up at a constant frame rate on a time-series basis. The image acquisition unit 144 may acquire images input from the input unit 120 or images stored in a storage unit 162. Further, the image acquisition unit 144 may acquire images from an external device, such as a server, connected to a network (not shown).

The image recognition unit 146 (an example of an endoscopic image recognition device) recognizes the images, which are acquired by the image acquisition unit 144, using a learning model that is learned by the endoscopic image learning device 10. In this embodiment, the image recognition unit 146 classifies whether or not a treatment tool is present from the images acquired by the image acquisition unit 144.

A display control unit 158 causes the display unit 118 to display the images generated by the image processing unit 142. Further, the display control unit 158 may cause the display unit 118 to display the results of classification of whether or not a treatment tool is present that is performed by the image recognition unit 146.

A storage control unit 160 causes the storage unit 162 to store the images that are generated by the image processing unit 142. For example, the storage control unit 160 causes the storage unit 162 to store images that are picked up according to an instruction to acquire a static image, information about the wavelength patterns of the irradiation light L0 at the time of the pickup of images, and the like.

The storage unit 162 is, for example, a storage device, such as a hard disk drive. The storage unit 162 is not limited to a storage unit built in the processor device 116. For example, the storage unit 162 may be an external storage device (not shown) connected to the processor device 116. The external storage device may be connected through a network (not shown).

The endoscope system 100 formed as described above normally takes videos at a constant frame rate, and displays the picked-up images on the display unit 118. Further, the endoscope system 100 classifies whether or not a treatment tool is present from the taken videos, and displays the results of classification on the display unit 118.

According to the endoscope system 100, since an endoscopic image is recognized by the image recognition unit 146 that uses a learning model learned by the endoscopic image learning device 10, an image can be appropriately recognized.

ADDITIONAL REMARKS

Configuration to be described below is also included in the scope of the invention in addition to the aspects and examples having been described above.

Additional Remark 1

A medical image processing device comprising:

a medical image-analysis processing unit (image recognition unit) that detects a region of interest, which is a region to be noticed, on the basis of the feature quantity of pixels of a medical image (endoscopic image); and a medical image-analysis result acquisition unit that acquires an analysis result of the medical image-analysis processing unit.

Additional Remark 2

A medical image processing device comprising:

a medical image-analysis processing unit (image recognition unit) that detects whether or not an object to be noticed is present on the basis of the feature quantity of pixels of a medical image; and a medical image-analysis result acquisition unit that acquires an analysis result of the medical image-analysis processing unit.

Additional Remark 3

The medical image processing device, wherein the medical image-analysis result acquisition unit (image recognition unit) acquires the analysis result from a recording device recording an analysis result of the medical image, and the analysis result includes any one or both of the region of interest that is the region to be noticed included in the medical image and whether or not the object to be noticed is present.

Additional Remark 4

The medical image processing device, wherein the medical image is a normal light image that is obtained from the application of light in a white-light wavelength range or light in a plurality of wavelength ranges as the light in a white-light wavelength range.

Additional Remark 5

The medical image processing device, wherein the medical image is an image that is obtained from the application of light in a specific wavelength range, and the specific wavelength range is a range narrower than the white-light wavelength range.

Additional Remark 6

The medical image processing device,
wherein the specific wavelength range is a blue-light wavelength range or a green-light wavelength range of a visible-light wavelength range.

Additional Remark 7

The medical image processing device,
wherein the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

Additional Remark 8

The medical image processing device,
wherein the specific wavelength range is a red-light wavelength range of a visible-light wavelength range.

Additional Remark 9

The medical image processing device,
wherein the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

Additional Remark 10

The medical image processing device,
wherein the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

Additional Remark 11

The medical image processing device,
wherein the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

Additional Remark 12

The medical image processing device,
wherein the medical image is an in-vivo image of the inside of a living body, and the in-vivo image includes information about the fluorescence of a fluorescent material present in the living body.

Additional Remark 13

The medical image processing device,
wherein the fluorescence is obtained from the application of excitation light, which has a peak wavelength in a wavelength range of 390 nm to 470 nm, to the inside of the living body.

Additional Remark 14

The medical image processing device,
wherein the medical image is an in-vivo image of the inside of a living body, and the specific wavelength range is an infrared wavelength range.

Additional Remark 15

The medical image processing device,
wherein the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

Additional Remark 16

The medical image processing device,
wherein a medical image acquisition unit comprises a special-light-image acquisition section that acquires a special light image including information about the specific wavelength range on the basis of a normal light image obtained from the application of light in a white-light wavelength range or light in a plurality of wavelength ranges as the light in a white-light wavelength range, and
the medical image is the special light image.

Additional Remark 17

The medical image processing device,
wherein a signal in the specific wavelength range is obtained from an arithmetic operation based on color information about red, green, and blue (RGB) or cyan, magenta, and yellow (CMY) included in the normal light image.

Additional Remark 18

The medical image processing device further comprising:
a feature-quantity-image generation section generating a feature quantity image from an arithmetic operation based on at least one of the normal light image that is obtained from the application of light in a white-light wavelength range or light in a plurality of wavelength ranges as the light in a white-light wavelength range or the special light image that is obtained from the application of light in a specific wavelength range,
wherein the medical image is the feature quantity image.

Additional Remark 19

An endoscope apparatus comprising:
the medical image processing device according to any one of Additional remarks 1 to 18; and
an endoscope that acquires an image from the application of at least one of light in a white-light wavelength range or light in the specific wavelength range.

Additional Remark 20

A diagnosis support apparatus comprising:
the medical image processing device according to any one of Additional remarks 1 to 18.

Additional Remark 21

A medical service support apparatus comprising:
the medical image processing device according to any one of Additional remarks 1 to 18.

OTHERS

In the embodiments described above, for example, the hardware structures of processing units, which perform various kinds of processing of the endoscopic image learning device 10, are various processors to be described below. Various processors include: a central processing unit (CPU) that is a general-purpose processor functioning as various processing units by executing software (program); a graphics processing unit (GPU) that is a processor specialized for image processing; a programmable logic device (PLD) that is a processor of which the circuit configuration can be changed after manufacture, such as a field programmable gate array (FPGA); a dedicated electrical circuit that is a processor having circuit configuration designed exclusively to perform specific processing, such as an application specific integrated circuit (ASIC); and the like.

One processing unit may be formed of one of these various processors, or may be formed of a combination of two or more same kind or different kinds of processors (for example, a plurality of FPGAs, a combination of a CPU and an FPGA, or a combination of a CPU and a GPU). Further, a plurality of processing units may be formed of one processor. As an example where a plurality of processing units are formed of one processor, first, there is an aspect where one processor is formed of a combination of one or more CPUs and software as typified by computers, such as a server and a client, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of various processors as hardware structures.

Furthermore, the hardware structures of these various processors are more specifically electrical circuitry where circuit elements, such as semiconductor elements, are combined.

The technical scope of the invention is not limited to the scopes described in the above-mentioned embodiments. The components and the like of the respective embodiments can be appropriately combined with each other without departing from the scope of the invention.

EXPLANATION OF REFERENCES

10: endoscopic image learning device
12: communication unit
14: foreground-material image database
14A: foreground-material image
16: background-endoscopic image database
16A: background image
16B: correct answer data
18: learning-endoscopic image database
20: operation unit
28: display unit
30: foreground image acquisition unit
30A: foreground image
32: image cut-out section
34: image processing section
36: background image acquisition unit
36A: background-endoscopic image
38: image generation unit
38A: superimposed image
38B: correct answer data
40: learning-endoscopic image acquisition unit
40A: learning-endoscopic image
40B: correct answer data
50: machine learning unit
52A: input layer
52B: intermediate layer
52C: output layer
54: error calculation section
56: parameter update section
100: endoscope system
102: endoscope
102A: insertion part
102B: operation part
102C: bendable part
102D: distal end part
102E: angle knob
102F: cap
103: mode changeover switch
104: forceps port
105: forceps outlet
106: air/water supply nozzle
107: observation window
108: illumination window
114: light source device
116: processor device
118: display unit
120: input unit
122A: first laser light source
122B: second laser light source
124: light source control unit
128A: optical fiber
128B: optical fiber
130: fluorescent body
132: diffusion member
134: image pickup lens
136: image pickup element
137: image pickup unit
138: analog/digital conversion unit
140: image pickup control unit
142: image processing unit
144: image acquisition unit
146: image recognition unit
158: display control unit
160: storage control unit
162: storage unit

What is claimed is:

1. An endoscope system comprising:
an endoscope including a distal end part having an image pickup element and a forceps outlet from which a treatment tool is protruded; and
one or more processors configured to:
acquire an endoscopic image through the image pickup element; and
perform a recognition process of the endoscopic image using a learning model that is learned by a machine learning process using a plurality of superimposed images in which a foreground image including an image of the treatment tool is superimposed on a background image that is an image of a living body,
wherein at least one of followings: presentation of the treatment tool in the endoscopic image, a type of the treatment tool in the endoscopic image, and an area of the treatment tool in the endoscopic image is recognized in the recognition process.

2. The endoscope system according to claim 1, further comprising a display,
wherein the one or more processors are further configured to display a result of the recognition on the display.

3. The endoscope system according to claim 2, wherein the one or more processors are further configured to display the endoscopic image.

4. The endoscope system according to claim 1, wherein:
the endoscope includes an insertion part having a bendable part at a distal end side of the insertion part; and
the distal end part is positioned at a distal end side of the bendable part.

5. The endoscope system according to claim 1, wherein the foreground image is processed by a specific processing step.

6. The endoscope system according to claim 5, wherein the specific processing step is at least one of an affine transformation processing step, a color conversion processing step, or a noise application processing step.

7. The endoscope system according to claim 1, wherein the foreground image is generated by cutting out the image of the treatment tool from a foreground-material image including the image of the treatment tool.

8. The endoscope system according to claim 7, wherein the foreground-material image is an endoscopic image that is picked up in a case where the treatment tool is utilized in the endoscope.

9. The endoscope system according to claim 7, wherein the foreground-material image is an image other than an endoscopic image.

10. The endoscope system according to claim 1, wherein the learning model includes a convolution neural network.

11. The endoscope system according to claim 1, wherein the one or more processors are further configured to:
  generate the superimposed images; and
  perform the learning process of the learning model through utilizing the superimposed images.

12. The endoscope system according to claim 11, wherein the specific processing step is at least one of an affine transformation processing step, a color conversion processing step, or s noise application processing step.

13. The endoscope system according to claim 11, wherein the one or more processors are configured to perform the learning process through utilizing a convolution neural network.

14. The endoscope system according to claim 1, wherein the learning model is learned using a label assigned to the treatment tool in the superimposed images.

15. The endoscope system according to claim 1, wherein the learning model performs segmentation to distinguish between the area of the treatment tool and areas other than the area of the treatment tool.

16. The endoscope system according to claim 1, wherein the superimposed images include a plurality of images with different positions of the treatment tool in the image.

17. The endoscope system according to claim 1, wherein the superimposed images include an image obtained by superimposing different types of treatment tools.

18. The endoscope system according to claim 17, wherein the one or more processors are configured to recognize multiple types of treatment tools using the learning model.

19. The endoscope system according to claim 18, wherein:
  the endoscope includes an insertion part having a bendable part at a distal end side of the insertion part; and
  the distal end part is positioned at a distal end side of the bendable part.

* * * * *